United States Patent [19]

Donn

[11] Patent Number: 5,623,782
[45] Date of Patent: Apr. 29, 1997

[54] MAIZE RESISTANT TO ARYLOXYPHENOXYALKANECARBOXYLIC ACID HERBICIDES

[75] Inventor: Günter Donn, Hofheim am Taunus, Germany

[73] Assignee: Hoechst Aktiengesellschaft, Frankfurt, Germany

[21] Appl. No.: 458,734

[22] Filed: Jun. 2, 1995

Related U.S. Application Data

[62] Division of Ser. No. 245,064, May 17, 1994, abandoned, which is a continuation of Ser. No. 70,430, filed as PCT/EP92/00506, Mar. 7, 1992, abandoned.

[30] Foreign Application Priority Data

Mar. 12, 1991 [EP] European Pat. Off. ............. 91103765

[51] Int. Cl.$^6$ ................. A01H 1/04; A01H 1/06; C12N 5/04; C12N 15/01
[52] U.S. Cl. ................. 47/58; 800/200; 800/235; 800/230; 800/DIG. 58
[58] Field of Search .................. 800/200, 235, 800/230, DIG. 56; 47/58

[56] References Cited

U.S. PATENT DOCUMENTS

| | | | |
|---|---|---|---|
| 5,145,777 | 9/1992 | Goodman et al. | 435/172.3 |
| 5,162,602 | 11/1992 | Somers et al. | 800/235 |
| 5,502,271 | 3/1996 | Donn | 800/200 |

OTHER PUBLICATIONS

Proc. Natl. Acad., Sci. USA, vol. 87, pp. 7175–7179, "Dominant Mutations Causing Alterations in Acetyl–Coenzyme Carboxylase Confer Tolerance to Cyclohexanedione and Aryloxyphenoxypropionate Herbicides in Maizer", Parker et al.

Pesticide Biochemistry and Physiology 24, pp. 298–305 (1985), "Inhibition of Fatty Acid Biosynthesis in Isolated Bean and Maize Chloroplasts by Herbicidal Phenoxy–phenoxypropionic acid Derivatives and Structurally Related Compounds", Hoppe et al.

Agrochemicals, vol. 112, 1990, p. 285.

Gronwald et al., 1989, Brighton Crop Protection Conference Weeds, p. 1217–1224.

Olson et al., 1988, In Corn and Corn Improvement. Sprague et al., eds., pp. 674–676 & 639.

Gordon-Kamm et al., The Plant Cell, vol. 2, pp. 603–618.

*Primary Examiner*—David T. Fox
*Assistant Examiner*—Thomas Haas
*Attorney, Agent, or Firm*—Curtis, Morris & Safford, P.C.

[57] ABSTRACT

By selection for resistance to aryloxyphenoxyalkanecarboxylic acid herbicides, herbicide-tolerant maize cell lines, calli and plants regenerated therefrom can be obtained which pass this herbicide tolerance on to their progeny in a stable manner.

3 Claims, No Drawings

1

MAIZE RESISTANT TO ARYLOXYPHENOXYALKANECARBOXYLIC ACID HERBICIDES

This application is a division of application Ser. No. 08/245,064, filed May 17, 1994, now abandoned, which is a continuation of Ser. No. 08/070,430, filed Jun. 8, 1993, now abandoned, which is the National Phase of PCT/EP92/00506, filed Mar. 7, 1992, designating the U.S.

BACKGROUND OF THE INVENTION

Aryloxyphenoxyalkanecarboxylic acid herbicides (which are also to be understood as meaning heteroaryloxyphenoxyalkanecarboxylic acid derivatives) are effective grass herbicides. A representative of this class of active substances which is to be mentioned hereinafter is fenoxaprop-ethyl ("FOPE"), which is to be understood as meaning the biologically active D-isomer as well as the racemate. They act on plants from the family of the Poaceae (Gramineae), since only this plant family has a specific form of acetyl coenzyme A carboxylase (ACC) which can be inhibited by micromolar concentrations of FOPE. Remaining terrestrial plants have ACC types whose sensitivity to this class of active substances is 100 to 1000 times lower.

Since FOPE and other aryloxyphenoxyalkanecarboxylic acid herbicides are taken up via the aerial parts of the plants, but are rapidly inactivated in the soil, these herbicides are suitable for controlling grasses post-emergence.

The crop plant maize (*Zea mays*) is particularly sensitive to FOPE. This is why these compounds cannot be used for controlling grass weeds in maize fields.

It has been found that in areas where FOPE has been applied repeatedly, forms arise spontaneously in populations of wild grasses which are resistant to this class of herbicide. Since such mutations occur only at a rate of approximately $10^{-7}$ to $10^{-9}$, a corresponding search for mutants in maize fields would be of little promise even if maize were not so highly sensitive to FOPE.

SUMMARY OF THE INVENTION

Surprisingly, it has now been found that maize cells can be selected which are resistant to FOPE and which can be grown on to give resistant plants which, in turn, pass on this resistance property in a stable manner.

DESCRIPTION OF THE PREFERRED EMBODIMENTS

Cell lines which are suitable for selection are known (for example from Morocz et al., Theor. Appl. Genet. 80 (1990) 721–726) or have been proposed in European Patent Applications 90 111 945.3 and 90 111 946.1. With effect from Sep. 30, 1990, a suitable cell line was deposited at the Deutsche Sammlung yon Mikroorganismen und Zellkulturen [German Collection of Microorganisms and Cell Cultures] in compliance with the provision of the Budapest treaty, Deposit No. DSM 6009.

To obtain resistant cell lines, the cells are cultured in auxin-free media in the presence of FOPE concentrations which kill more than 90% of the cells. The cells can be cultured in such media for as long as desired, for example easily over 10 transfers and more. Synthetic auxins, such as 2,4-dichlorophenoxyacetic acid, p-chlorophenoxyacetic acid, 2,4,5-trichlorophenoxyacetic acid and 3,6-dichloro-2-methoxybenzoic acid (dicamba) antagonize the effect of FOPE if the latter is employed in sublethal concentrations.

Selection experiments using FOPE in the concentration range of up to $10^{-5}M$ in the presence of synthetic auxins were unsuccessful. This is why auxin-autotrophic maize cell lines were used.

It is characteristic of auxin-autotrophic cell lines that they can, in the form of an embryogenic culture, be subcultured on phytohormone-free cell culture media for as long as desired, for example for two to three years. Auxin-autotrophic calli were subcultured in each case every 3 to 4 weeks over 15 transfers and more, and mutants were found by stepwise increase of the FOPE concentration. These FOPE-tolerant mutants can be sub-cultured over 10 transfers and more on FOPE-containing, auxin-free medium. Under selective conditions, i.e. in the presence of $10^{-4}M$ FOPE, the embryogenic calli spontaneously give rise to plants which can be grown on to give fertile maize plants.

Flowering regenerated plants are, on the one hand, selfed and, on the other hand, pollen from the regenerated plants is used for pollinating inbred lines. The mature seeds are sown, and the $F_1$ generation seedlings are treated with FOPE when they have reached the 2- to 4-leaf stage. A considerable number of selected plants survive even at concentrations of up to 200 g of active substance per ha (g of a.i./ha).

The regenerated maize plants can be treated with FOPE at rates of up to 200 g of a.i./ha; it is preferred to employ between 20 and 150 g, in particular between 30 and 90 g, of a.i./ha. These amounts apply to the biologically active D-isomer of fenoxaprop-ethyl. Maize plants according to the invention are preferably selected using the optically active isomer, but suitable amounts of the racemate can also be employed.

The ACC gene can be isolated from the mutants according to the invention and characterized in a manner known per se. Mutated genes, which encode FOPE-tolerant ACC, can be used for the transformation of other plant cells.

It is furthermore possible to combine FOPE tolerance in maize with resistance to other herbicides. To this end, for example, transgenic cell lines are used which contain a resistance gene for the non-selective herbicide phosphinothricin, glufosinate or bialaphos. Such genes are disclosed, for example, in EP-A 0,257,542, 0,275,957, 0,297,618 or from DE-A 3,701,623 or DE-B 3,825,507. When suitable cell lines are grown, phosphinothricin tolerance can be employed as an additional marker.

Other transgenic plants according to the invention may contain toxin genes, for example genes encoding the δ-endotoxin of *Bacillus thuringiensis*, or genes for chitinases or glucanases, or other selectable marker genes, for example genes for resistance to glyphosate or sulfonylureas.

The following ($C_1$-$C_4$)alkyl, ($C_2$-$C_4$)alkenyl and ($C_3$-$C_4$) alkynyl aryloxyphenoxyalkanecarboxylate herbicides can also be employed for selecting resistant maize cell lines:

A1) Phenoxyphenoxy- and benzyloxyphenoxyalkanecarboxylic acid derivatives, for example methyl 2-(4-(2,4-dichlorophenoxy)phenoxy)propionate (diclofop-methyl), methyl 2-(4-(4-bromo-2-chlorophenoxy)phenoxy) propionate (see DE-A-2,601,548), methyl 2-(4-(4-bromo-2-fluorophenoxy)phenoxy) propionate (see U.S. Pat. No. 4,808,750), methyl 2-(4-(2-chloro-4-trifluoromethylphenoxy) phenoxy)propionate (see DE-A-2,433,067), methyl 2-(4-(2-fluoro-4-trifluoromethylphenoxy) phenoxy)propionate (see U.S. Pat. No. 4,808,750), methyl 2-(4-(2,4-dichlorobenzyl)phenoxy)propionate (see DE-A-2,417,487), ethyl 4-(4-(4-trifluoromethylphenoxy)phenoxy)pent-2-enoate, methyl 2-(4-(4-trifluoromethylphenoxy)phenoxy) propionate (see DE-A-2,433,067), A2) "Mononuclear" heteroaryloxyphenoxyalkanecarboxylic acid derivatives, for example ethyl 2-(4-(3,5-dichloropyridyl-2-oxy)phenoxy) propionate (see EP-A-2,925), propargyl 2-(4-(3,5-dichloropyridyl-2-oxy)phenoxy) propionate (EP-A-3,114), methyl 2-(4-(3-chloro-5-trifluoromethyl-2-pyridyloxy) phenoxypropionate (see EP-A-3,890), ethyl 2-(4-(3-chloro-5-trifluoromethyl-2-pyridyloxy) phenoxy)propionate (see EP-A-3,890), propargyl 2-(4-(5-chloro-3-fluoro-2-pyridyloxy) phenoxy)propionate propionate (EP-A-191,736), butyl 2-(4-(5-trifluoromethyl-2-pyridyloxy) phenoxypropionate (fluazifop-butyl; fusilade-butyl), A3) "Binuclear" heteroaryloxyphenoxyalkanecarboxylic acid derivatives, for example methyl and ethyl 2-(4-(6-chloro-2-quinoxalyloxy) phenoxy)propionate (quizalofop-methyl and -ethyl), methyl 2-(4-(6-fluoro-2-quinoxalyloxy)phenoxy) propionate (see J. Pest. Sci. Vol. 10, 61 (1985)), methyl and 2-isopropylideneaminooxyethyl 2-(4-(6-chloro-2-quinolyloxy)phenoxy)propionate (propaquizafop and its ester), ethyl 2-(4-(6-chlorobenzoxazol-2-yloxy)phenoxy) propionate (fenoxaprop-ethyl) and ethyl 2-(4-(6-chlorobenzothiazol-2-yloxy) phenoxypropionate (see DE-A-2,640,730)).

The auxin-autotrophic cell lines are also particularly suitable for the selection of mutants which are obtained using other ACC-inhibitors, namely cyclohexanedione-herbicides, in particular sethoxydim, tralkoxydim, cycloxydim, alloxydim and clethoxydim.

The fact that maize plants can be obtained which are resistant to conventional concentrations of sethoxydim has been published by Parker et al. (Proc. Natl. Acad. Sci. Vol. 87, pp. 7175–7179). These plants also display a certain cross-resistance to low concentrations of haloxyfop. However, the maize plants produced according to the invention are resistant to higher concentrations of aryloxyphenoxyalkanecarboxylic acid herbicides, as they are required for use in practice. Thus, the maize plants according to the invention allow the selective control of monocotyledon weeds (grass weeds) in maize using aryloxyphenoxyalkanecarboxylic acid derivatives (including heteroaryloxyphenoxyalkanecarboxylic acid derivatives), either alone or in combination with each other.

The invention also relates to the use of maize plants which are treated with a combination of aryloxyphenoxycarboxylic acid herbicides and herbicides against dicotyledon weeds. This is because it was possible, surprisingly, to identify components for mixtures for aryloxyphenoxyalkanecarboxylic acid herbicides which are not only tolerated by the regenerated maize plants, but whose herbicidal activity is simultaneously improved.

Thus, the combination of the herbicides results in synergistic effects. Using such mixtures means substantial economical, but also ecological, advantages.

Synergism is to be understood as meaning a mutually reinforcing effect of two or even more substances. In the present case, the combined use of two herbicides allows the application rate of the herbicides to be reduced while still achieving the same herbicidal activity, or, using the same application rates of the herbicides allows a higher activity to be achieved than to be expected on the basis of the individually employed active substances.

By using such synergistic effects, it is possible to considerably reduce the application rates of the components involved in the mixture, and a broad range of mono- and dicotyledon weeds can be controlled in one operation. The reduced application rates apply in particular to the ACC-inhibitors, but also to the components in the mixtures with regard to effectiveness against dicotyledon weeds.

Particularly interesting from amongst the aryloxyphenoxyalkanecarboxylic acid herbicides are the following herbicides: fenoxaprop-ethyl, haloxyfop-methyl, quizalofop-ethyl, fluazifop-butyl.

The following herbicides display synergistic activity when used as a component in mixtures for the additional control of broad-leaf weeds:

Primisulfuron, thifensulfuron, nicosulfuron, DPX-E 9636, amidosulfuron, pyridylsulfonylureas, as described in German Patent Applications P 4,000,503.8 and P 4,030, 577.5, in particular 3-(4,6-dimethoxypyrimidin-2-yl)-1-[3-(N-methyl-N-methylsulfonylamino-2-pyridylsulfonyl]urea, an alkoxyphenoxysulfonylurea, as described in EP-A-0,342, 569, furthermore NC 319 (EP 282,613) and other sulfonylureas, as well as mixtures of various abovementioned sulfonylureas with each other, such as, for example, a mixture of nicosulfuron and DPX-E 9636.

Other herbicides which have the same, or a similar, mechanism of action as the above sulfonylureas, namely imidazolinones, such as, for example, imazethapyr, imazaquin, imazapyr (each of which can be employed in maize together with a safener), also display a synergistic increase in activity when employed together with ACC inhibitors.

Other herbicides which, like sulfonylureas and imidazolinones, are inhibitors of the enzyme acetolactate synthase (ALS) are also suitable, for example substituted pyrimidines and triazines, herbicidal sulfonamides, such as flumetsulam (Cordes, R. C. et al., Abstr. Meet. Weed Sci. Soc. Am. 31, 10, 1991), or other related compounds and mixtures of such active substances with each other.

A series of other herbicides which are employed for controlling weeds in maize, but display different mechanisms of action, also showed a synergistic increase in activity when used together with fenoxaprop-ethyl or with other ACC inhibitors:

ICI-051: (2-[2-chloro-4-(methylsulfonyl)benzoyl]-1,3-cyclohexanedione, atrazine, cyanazine and terbuthylazine, clopyralid, pyridate, bromoxynil, pendimethalin, dicamba.

The herbicides are generally used at application rates of between 0.01 and 2 kg/ha, i.e. the total amount of active substance combination to be used is approximately 0.05 to 2 kg/ha. The application rate required can vary as a function of the external conditions, such as temperature and humidity, inter alia, that is preferably between 0.05 and 1 kg/ha. The ratios of the components can vary within wide limits. A quantitative ratio of between 1:20 and 20:1 is preferably selected.

These synergistic effects are achieved not only in the case of mixtures with fenoxaprop-ethyl, but also when other ACC inhibitors are used, for example the cyclohexanediones. A combination of the active substances is to be understood as meaning that the herbicidal active substances are applied together or one after the other, at an interval of a few days, in the form of a so-called split application. In each case the weeds respond with an increased sensitivity, so that lower application rates allow a very good control effect.

In the following examples, the invention will be illustrated in greater detail without being restricted thereto. Percentages relate to the weight, unless otherwise specified.

EXAMPLE 1

Selection of FOPE-tolerant Embryogenic Maize Cell Cultures

Maize plants from inbred lines B 73 and LH 82 were pollinated with pollen from genotype HE 89, which is capable of regeneration (Morocz et al., Theor. Appl. Genet. 80 (1990) 721–726 loc. cit.). 12 to 14 days after pollination, immature embryos were dissected from the seeds under sterile conditions and grown on hormone-free $N_6$ culture medium (Chu et al., Sci. Sin. 18 (1975) 659–668) containing 9% of sucrose, the embryo axis being in contact with the medium. Within 3 to 4 weeks, embryogenic callus was formed on approximately 25% of the embryos, 1.0 to 2.0 mm in size, and this embryogenic callus could be subcultured on hormone-free medium. After 3 to 4 subcultures, the selection of FOPE-tolerant mutants was started using the callus lines which were distinguished by vigorous growth and reproducible differentiation of somatic embryos on the hormone-free medium.

Alternatively, callus lines were cultured, with 3 to 4 transfers, on $N_6$ medium containing 1 mg/l of 2,4-dichlorophenoxyacetic acid (2,4-D). The callus sectors consisting of undifferentiated cells were used for subculturing. From these callus sectors, suspension cultures could be induced which were cultured in liquid $N_6$ medium containing 0.5 mg/l of 2,4-D and transferred weekly to fresh medium.

Tissue was taken from both callus cultures and suspension cultures and incubated for 4 to 6 weeks on hormone-free $N_6$ medium in the presence of $1-3\times10^{-6}M$ FOPE. Under these conditions, up to approximately 95% of the cells and cell clusters were killed.

The surviving cell clusters were grown on on hormone-free $N_6$ medium containing $3\times10^{-6}M$ FOPE, by means of 2 transfers. Per transfer, the cells remained on the selection medium for 4 to 6 weeks.

Subclones growing equally well under these conditions as wild-type cells on FOPE-free medium were grown on on hormone-free $N_6$ medium containing $1\times10^{-5}M$ FOPE.

After a further 4 to 6 weeks, those clones which continued to grow on this selection medium without significant loss of vitality were transferred to a medium containing $3\times10^{-5}M$ FOPE and, during the following subculturing, transferred to hormone-free $N_6$ medium containing $1\times10^{-4}M$ active substance. Higher active substance concentrations did not improve the selection effect further since the active substance crystallizes in the medium at a concentration of as little as $3\times10^{-5}M$.

EXAMPLE 2

Regeneration of FOPE-tolerant Plants

Plants which have been regenerated from those mutated clones which grew in the presence of $1\times10^{-4}N$ FOPE in hormone-free $N_6$ medium for 3 to 10 transfers without reduced vitality, differentiating plants from somatic embryos in the process, were transferred into soil and grown in a controlled-environment cabinet at 30,000 to 40,000 Lux, a daytime temperature of $23°\pm1°$ C. and a night-time temperature of $16°\pm1°$ C., with an illumination period of 14 hours. When the plants have developed 4 to 5 leaves, they are sprayed with 30 g of FOPE per ha. The plants survived this treatment without significant damage, while control plants were killed by the herbicide at this dosage rate.

The flowering regenerated plants were, on the one hand, selfed and, on the other hand, their pollen was used for pollinating inbred lines, such as, for example, B 73, LH 51, LH 82, LH 119, KW 1292, KW 5361, RA 1298 or RA 3080. The mature seeds were sown, and the $F_1$ generation seedlings treated with FOPE when they had reached the 2- to 4-leaf stage. The results are given in Table 1.

TABLE 1

Treatment of regenerated plants and progeny with FOPE (* und. = undamaged)

| Plants | Number | FOPE treatment 15 g of a.i./ha dead plants/ und.* | | 30 g of a.i./ha dead plants/ und.* | | 60 g of a.i./ha dead plants/ und.* | |
|---|---|---|---|---|---|---|---|
| Regen. plants of unselected controls | 20 | | | 20 | — | | |
| Regen. plants of resistant callus | 10 | | | — | 10 | | |
| Progeny from self-pollination | 60 (3 × 20) | 5 | 15 | 7 | 13 | 8 | 12 |
| $F_1$-progeny from crosses | 48 (3 × 16) | 8 | 8 | 10 | 6 | 7 | 9 |
| Commercial variety Felix | 48 | 16 | — | 16 | — | 16 | — |

EXAMPLE 3

Haloxyfop-tolerant Maize

Resistant maize cell lines were obtained by the process described in Examples 1 and 2 and examined for resistance to haloxyfop. It was found that cell lines according to the invention tolerate a markedly higher dosage rate than the maize cell lines known from the prior art (see Parker et al.).

EXAMPLE 4

Treatment of Herbicide-resistant Maize Plants with Synergistic Combinations of Herbicides FOPE-resistant maize plants obtained by the process described in Examples 1 and 2 were grown in the greenhouse in pots of diameter 9 cm together with grass weeds and broad-leaf weeds until they had reached the 4–6 leaf stage, when they were treated post-emergence with the herbicides according to the invention. A water volume of 400 l/ha was used, two replications were carried out, and, after 5 weeks, the plants were scored on a percentage key basis by visually assessing the control effect on the weeds.

The results from various experiments showed unexpected synergistic increases in effects by herbicidal combinations which had been applied either concomitantly or one shortly after the other (see Tables 2 and 3).

No damage of any kind was observed on the herbicide-resistant maize plants. Herbicides B4 and B6 were in each case both applied together with an active substance which acts as a safener.

TABLE 2

Herbicidal activity against grasses

| Herbicide | Dosage rate of g of AS/ha | % activity against ||||||
|---|---|---|---|---|---|---|---|
| | | SEVI | DISA | PAMI | ECCG | SOHA | ZEMA |
| A | 50 | 100 | 100 | — | — | — | 0 |
| | 25 | 100 | 99 | 100 | 100 | 98 | 0 |
| | 12 | 85 | 85 | 100 | 100 | 85 | 0 |
| | 6 | 60 | 50 | 80 | 99 | 40 | 0 |
| B1 | 50 | 98 | 93 | 65 | 98 | 60 | 0 |
| | 25 | 95 | 85 | 20 | 95 | 35 | 0 |
| | 12 | 85 | 75 | 10 | 80 | 25 | 0 |
| B2 | 12 | 0 | 10 | 0 | 0 | 20 | 0 |
| | 6 | 0 | 5 | 0 | 0 | 0 | 0 |
| B3 | 50 | 50 | 20 | 30 | 30 | 90 | 0 |
| | 25 | 40 | 10 | 0 | 20 | 80 | 0 |
| | 12 | 30 | 0 | 0 | 20 | 70 | 0 |
| B4 | 25 | 80 | 90 | 65 | 95 | 45 | 0 |
| | 12 | 70 | 85 | 40 | 90 | 30 | 0 |
| | 6 | 60 | 70 | 15 | 75 | 20 | 0 |
| B5 | 25 | 85 | 95 | 70 | 90 | 70 | 0 |
| | 12 | 80 | 90 | 40 | 80 | 50 | 0 |
| | 6 | 80 | 80 | 25 | 70 | 30 | 0 |
| B6 | 100 | 95 | 90 | 70 | 70 | 60 | 0 |
| | 50 | 80 | 80 | 60 | 70 | 40 | 0 |
| B7 | 250 | 5 | 0 | 0 | 10 | 0 | 0 |
| | 125 | 0 | 0 | 0 | 0 | 0 | 0 |
| B8 | 250 | 0 | 0 | 0 | 0 | 0 | 0 |
| | 125 | 0 | 0 | 0 | 0 | 0 | 0 |
| B9 | 250 | 0 | 0 | 0 | 5 | 0 | 0 |
| | 125 | 0 | 0 | 0 | 0 | 0 | 0 |
| A + B1 | 12 + 12 | 100 | 100 | 100 | 100 | 98 | 0 |
| | 12 + 25 | 100 | 98 | 95 | 100 | 80 | 0 |
| A + B2 | 12 + 12 | 100 | 100 | 100 | 100 | 99 | 0 |
| | 6 + 12 | 100 | 99 | 100 | 100 | 75 | 0 |
| A + B3 | 12 + 12 | 100 | 100 | 100 | 100 | 100 | 0 |
| | 12 + 25 | 100 | 100 | 100 | 100 | 100 | 0 |
| A + B4 | 12 + 12 | 100 | 100 | 100 | 100 | 99 | 0 |
| | 6 + 6 | 100 | 95 | 95 | 100 | 90 | 0 |
| A + B5 | 12 + 12 | 100 | 100 | 100 | 100 | 100 | 0 |
| | 6 + 6 | 100 | 98 | 98 | 100 | 100 | 0 |
| A + B6 | 12 + 50 | 100 | 100 | 100 | 100 | 100 | 0 |
| | 6 + 25 | 100 | 99 | 98 | 100 | 95 | 0 |
| A + B7 | 12 + 125 | 95 | 90 | 100 | 100 | 95 | 0 |
| A + B8 | 12 + 125 | 90 | 95 | 100 | 99 | 90 | 0 |
| A + B9 | 12 + 125 | 95 | 90 | 99 | 99 | 90 | 0 |

| Herbicide | Dosage rate of g of AS/ha | ABTH | CHAL | AMAR | POCO | AMRE | ZEMA |
|---|---|---|---|---|---|---|---|
| A | 50 | 0 | 0 | 0 | 0 | 5 | 0 |
| | 25 | 0 | 0 | 0 | 0 | 0 | 0 |
| | 12 | 0 | 0 | 0 | 0 | 0 | 0 |
| | 6 | 0 | 0 | 0 | 0 | 0 | 0 |
| B1 | 50 | 20 | 35 | 20 | 50 | 60 | 0 |
| | 25 | 10 | 20 | 10 | 30 | 50 | 0 |
| | 12 | 0 | 10 | 0 | 10 | 50 | 0 |
| B2 | 12 | 40 | 80 | 70 | 80 | 20 | 0 |
| | 6 | 20 | 60 | 40 | 50 | 10 | 0 |
| B3 | 50 | 70 | 80 | 30 | 40 | 40 | 0 |
| | 25 | 50 | 70 | 10 | 20 | 30 | 0 |
| | 12 | 40 | 50 | 0 | 20 | 15 | 0 |
| B4 | 25 | 20 | 95 | 85 | 80 | 80 | 0 |
| | 12 | 10 | 85 | 80 | 70 | 75 | 0 |
| | 6 | 0 | 50 | 70 | 70 | 60 | 0 |
| B5 | 25 | 30 | 80 | 75 | 30 | 60 | 0 |
| | 12 | 20 | 60 | 60 | 20 | 50 | 0 |
| | 6 | 10 | 40 | 40 | 10 | 30 | 0 |
| B6 | 100 | 60 | 40 | 70 | 50 | 80 | 0 |
| | 50 | 50 | 30 | 60 | 40 | 70 | 0 |
| B7 | 250 | 40 | 100 | 75 | 80 | 75 | 0 |
| | 125 | 15 | 85 | 40 | 50 | 30 | 0 |
| B8 | 250 | 70 | 95 | 70 | 85 | 65 | 0 |
| | 125 | 30 | 75 | 30 | 60 | 30 | 0 |
| B9 | 250 | 90 | 100 | 98 | 80 | 75 | 0 |
| | 125 | 75 | 80 | 70 | 40 | 60 | 0 |
| A + B1 | 12 + 12 | 40 | 50 | 30 | 60 | 90 | 0 |
| | 12 + 25 | 40 | 30 | 30 | 40 | 75 | 0 |

TABLE 2-continued

| Herbicidal activity against grasses | | | | | | | |
|---|---|---|---|---|---|---|---|
| A + B2 | 12 + 12 | 70 | 90 | 80 | 95 | 40 | 0 |
|  | 6 + 12 | 60 | 80 | 75 | 90 | 40 | 0 |
| A + B3 | 12 + 12 | 60 | 70 | 30 | 50 | 30 | 0 |
|  | 12 + 25 | 70 | 80 | 40 | 50 | 40 | 0 |
| A + B4 | 12 + 12 | 50 | 95 | 90 | 90 | 80 | 0 |
|  | 6 + 6 | 30 | 60 | 80 | 90 | 75 | 0 |
| A + B5 | 12 + 12 | 50 | 90 | 95 | 40 | 90 | 0 |
|  | 6 + 6 | 40 | 75 | 50 | 30 | 60 | 0 |
| A + B6 | 12 + 50 | 70 | 50 | 95 | 70 | 80 | 0 |
|  | 6 + 25 | 50 | 30 | 60 | 40 | 60 | 0 |
| A + B7 | 12 + 125 | 40 | 90 | 50 | 70 | 50 | 0 |
| A + B8 | 12 + 125 | 60 | 80 | 40 | 60 | 40 | 0 |
| A + B9 | 12 + 125 | 90 | 90 | 80 | 50 | 60 | 0 |

Key for Table

SEVI=*Setaria viridis* (green foxtail)
DISA=*Digitaria sanguinalis* (large crab grass)
PAMI=*Panicum miliaceum* (proso millet)
ECCG=*Echinochloa crus galli* (common barnyard grass)
SOHA=*Sorghum halepense* (Johnson grass)
ABTH=*Abutilon theophrasti* (velvetleaf)
CHAL=*Chenopodium album* (pigweed)
AMAR=*Ambrosia artemisifolia* (hogweed)
POCO=*Polygonum convolvulus* (black bindweed)
AMRE=*Amaranthus retroflexus* (red root pigweed)
ZEMA=*Zea mays* (maize)
A=Fenoxaprop-p-ethyl
B2=Nicosulfuron
B2=Thifensulfuron
B3=Primisulfuron
B4=3-(4,6-Dimethoxypyrimidin-2-yl)-1-[3-(N-methyl-N-methylsulfonylamino)-2-pyridylsulfonyl]urea
B5=DPX-9636
B6=Imazethapyr
B7=Atrazine
B8=Bromoxynil
B9=Dicamba

I claim:

1. A method for controlling mono- and dicotyledon weeds in cultures of maize plants which are resistant to aryloxyphenoxyalkanecarboxylic acid herbicides comprising applying to said plants aryloxyphenoxyalkanecarboxylic acid herbicides in combination with one or more herbicides selected from the group of the sulfonylureas and imidazolinones.

2. A method for controlling mono- and dicotyledon weeds in cultures of maize plants which are resistant to aryloxyphenoxyalkanecarboxylic acid herbicides comprising applying to said plants fenoxaprop-ethyl in combination with a sulfonylurea.

3. A method for controlling mono- and dicotyledon weeds in cultures of maize plants which are resistant to aryloxyphenoxyalkanecarboxylic acid herbicides comprising applying to said plants fenoxaprop-ethyl in combination with one or more herbicides selected from the group of the triazines, clopyralid, pyridate, bromoxynil, pendimethalin and dicamba.

* * * * *